US00PP15576P3

(12) United States Plant Patent

Richardson et al.

(10) Patent No.: US PP15,576 P3
(45) Date of Patent: Feb. 22, 2005

(54) BERMUDAGRASS HYBRID NAMED 'OZARK'

(50) Latin Name: *Cynodon dactylon*
Varietal Denomination: Ozark

(75) Inventors: William L. Richardson, Stillwater, OK (US); Charles M. Taliaferro, Stillwater, OK (US)

(73) Assignee: Oklahoma State University, Stillwater, OK (US)

( * ) Notice: Subject to any disclaimer, the term of this patent is extended or adjusted under 35 U.S.C. 154(b) by 0 days.

(21) Appl. No.: 10/346,221

(22) Filed: Jan. 17, 2003

(65) Prior Publication Data

US 2004/0111778 P1 Jun. 10, 2004

Related U.S. Application Data

(63) Continuation-in-part of application No. 10/310,226, filed on Dec. 5, 2002, now abandoned.

(51) Int. Cl.[7] ..... A01H 5/00
(52) U.S. Cl. ..... Plt./389
(58) Field of Search ..... Plt./389

(56) References Cited

PUBLICATIONS

Baker, "Ozarka Bermudagrass," *NF Ag News and Views*, The Samuel Roberts Noble Foundation, 20(1):4–5, 2002.
Bates et al., "Forage yields from bermudagrass varieties and strains," The Samuel Roberts Noble Foundation, Ardmore, OK.
Evers, "Performance of bermudagrass varieties in East Texas," Texas A&M University Agricultural Research & Extension Center, Overton.
Huneycutt, "Forage variety performance test," *Arkansas Agricultural Experiment Station*, Research Series 383, Apr. 1989.
Moyer and Taliaferro, "Forage production of bermudagrass cultivars in southeastern Kansas," Department of Agronomy, Oklahoma State University, Stillwater, 3–6.
Taliaferro and Pickard, "Bermudagrass performance trials," *Eastern Research Station Field Tour Proceedings*, 10–26, May 25, 1995.
Taliaferro et al., "Production technology—crops: Performance of forage bermudagrass varieties in Oklahoma tests, 1998–2002," Department of Plant and Soil Sciences, Division of Agricultural Sciences and Natural Resources, Oklahoma a State University, 1–13, 2003.
Taliaferro et al., "Production technology—crops: Performance of forage bermudagrass varieties in Oklahoma tests, 1998–2001," Department of Plant and Soil Sciences, Division of Agricultural Sciences and Natural Resources, Oklahoma State University, 1–10, 2002.
Taliaferro et al., "Production technology—crops: Performance of forage bermudagrass varieties in Oklahoma tests, 1998–2000," Department of Plant and Soil Sciences, Division of Agricultural Sciences and Natural Resources, Oklahoma State University, 1–7, 2001.
Taliaferro et al., "Production technology—crops: Performance of forage bermudagrass varieties in Oklahoma tests, 1995–1999," Department of Plant and Soil Sciences, Division of Agricultural Sciences and Natural Resources, Oklahoma State University, 1–11, 2000.
Taliaferro et al., "Production technology—crops: Performance of forage bermudagrass varieties in Oklahoma tests, 1992–1995," Department of Plant and Soil Sciences, Division of Agricultural Sciences and Natural Resources, Oklahoma State University, 8(9) 1–17, 1996.

*Primary Examiner*—Anne Marie Grunberg
*Assistant Examiner*—Annette H Para
(74) *Attorney, Agent, or Firm*—Fulbright & Jaworski L.L.P.

(57) ABSTRACT

The variety "Ozark" is a new and distinct hybrid bermudagrass variety. The plant was derived from an F1 hybrid cross of bermudagrass varieties A9959×"Coastal." "Ozark" has relatively tall, upright growth and exhibits superior cold tolerance relative to previous bermudgrass varieties, yielding well in the northern part of the bermudagrass belt.

5 Drawing Sheets

GENUS AND SPECIES NAME

The invention relates generally to the new and distinct variety of hybrid bermudagrass (*Cynodon dactylon* (L.) Pers.) described herein and designated "Ozark." As used herein, "Ozark" has the identical meaning as "Ozarka" in parent application Ser. No. 10/310,226, filed Dec. 5, 2002.

BACKGROUND OF THE INVENTION

The variety is an F1 hybrid progeny plant derived from the crossing of A9959×"Coastal" (each unpatented varieties) carried out in 1974 at the Oklahoma Agricultural Experimental Station, Oklahoma State University. "Ozark" has been asexually reproduced and the distinctive traits of the variety have remained stable. "Ozark" was first asexually reproduced at the Agronomy Research Station, Oklahoma State University, Stillwater, Okla.

Parent line A9959 is a bermudagrass introduction from Yugoslavia. The Georgia Coastal Plain Experiment Station and Plant Science Research Division of ARS released Coastal in 1943. Coastal is the F1 hybrid of "Tift" bermudagrass and a plant introduction from South Africa.

"Ozark" was selected from other bermudagrasses and evaluated for traits and characteristics as described herein. Initial field screenings identified "Ozark" as having desirable characteristics. This led to its inclusion in advanced multi-environmental performance tests. The results of certain of the analyses are presented herein below.

DETAILED DESCRIPTION OF THE VARIETY

"Ozark" is similar to "Midland," "Midland 99," and "Tifton 44" (all unpatented varieties) in morphology and growth habit. Like Midland 99 and Tifton 44, "Ozark" has relatively tall, upright growth in comparison to more decumbant cultivars such as "Greenfield." The stem diameter, shoot length, and leaf widths of Ozark, Midland, and Tifton 44 are similar. The leaves of "Ozark" tend to be longer than those of Midland and Tifton 44. "Ozark" typically produces inflorescences later and less profusely than Midland or Tifton 44. Like most hybrid bermudagrasses, "Ozark" sets only a few seeds and therefore must be propagated vegetatively.

Figure 1:
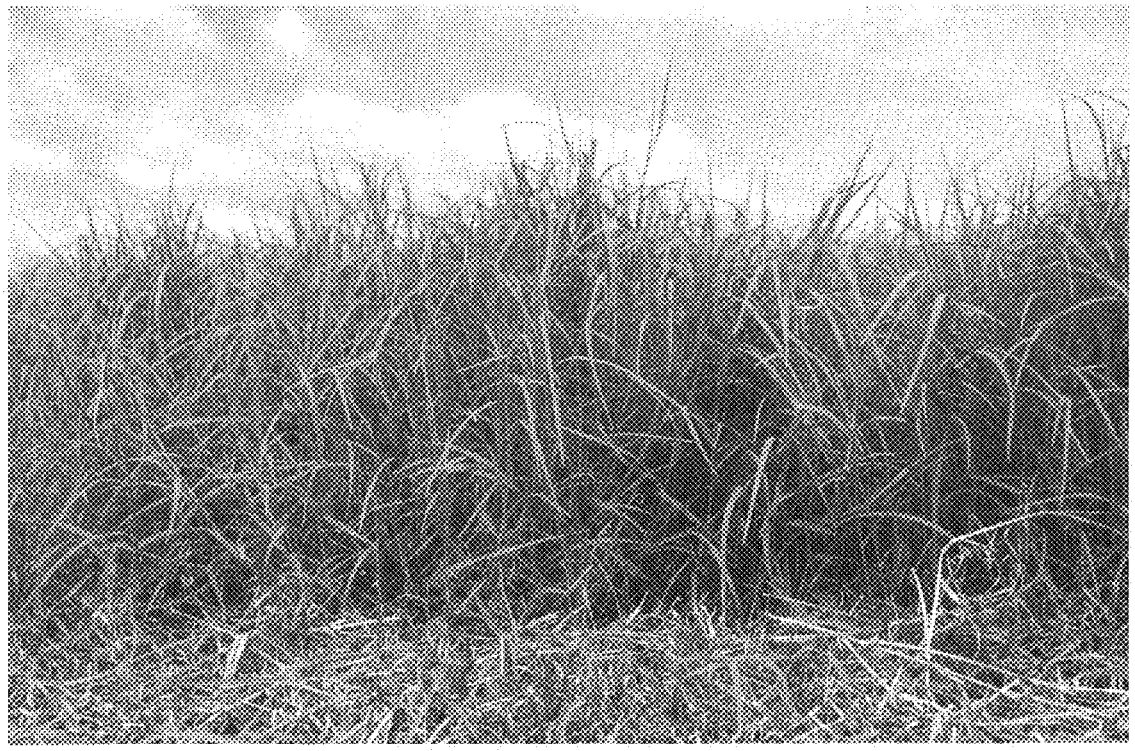
FIG. 1: "Ozark" bermudagrass fully established and ready for harvest. Note: complete ground cover at least 18 months after sprigging.
Figure 2:
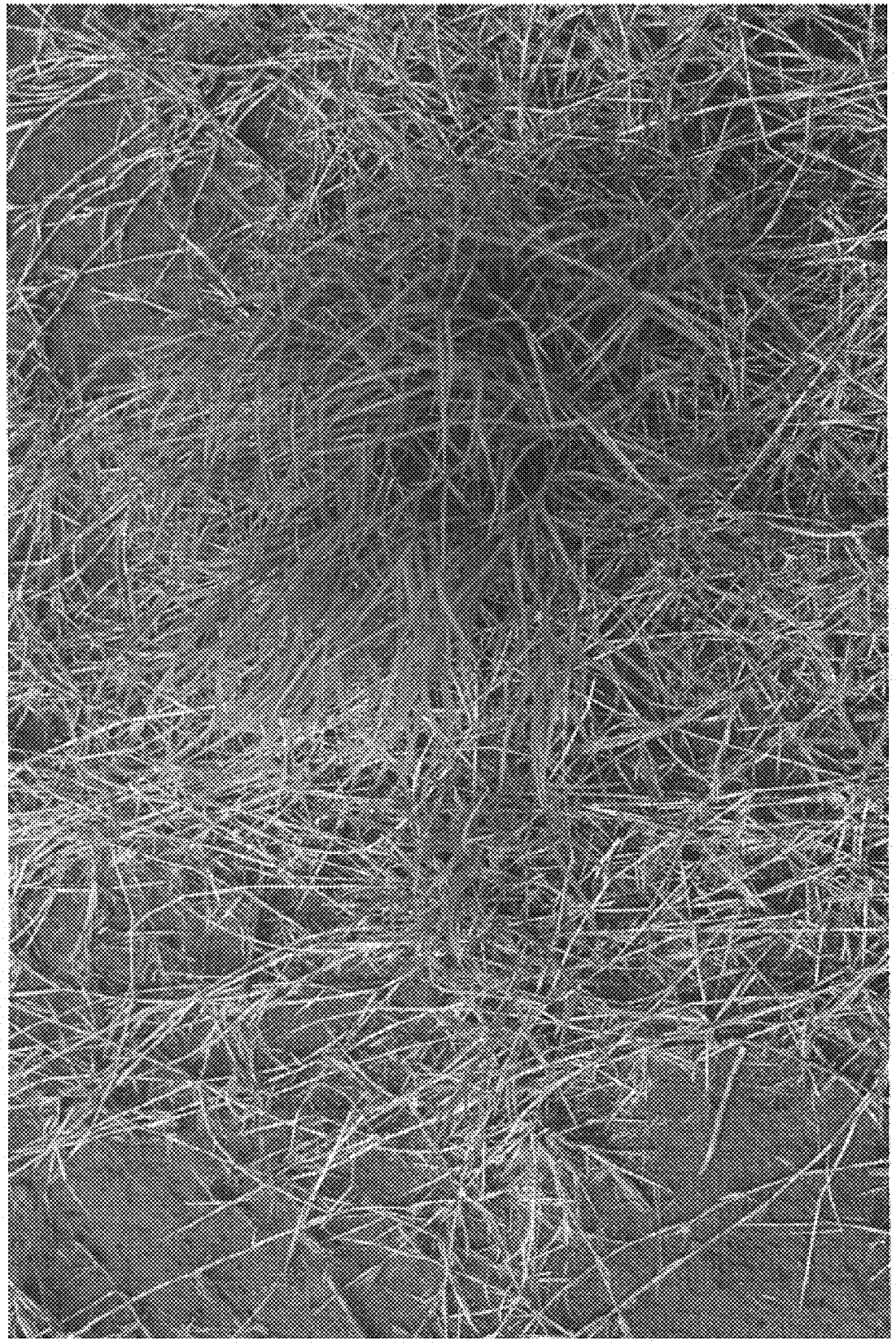
FIG. 2: Individual plant of "Ozark" bermudagrass. Note: Stoloniferious reproduction from main plant.
Figure 3:
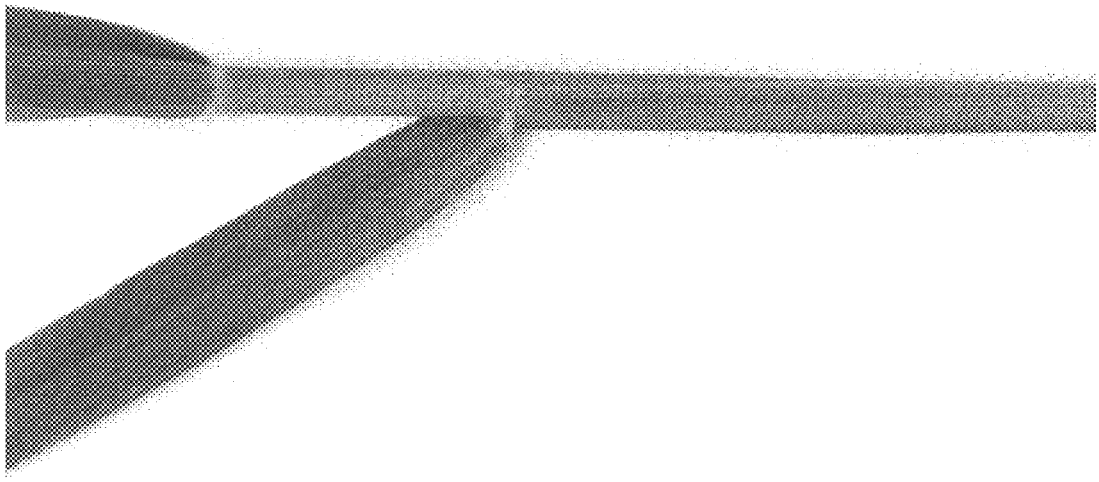
FIG. 3: Collar region of "Ozark" bermudagrass. Note: small pubescence where the leaf sheath and leaf blade meet.
Figure 4:
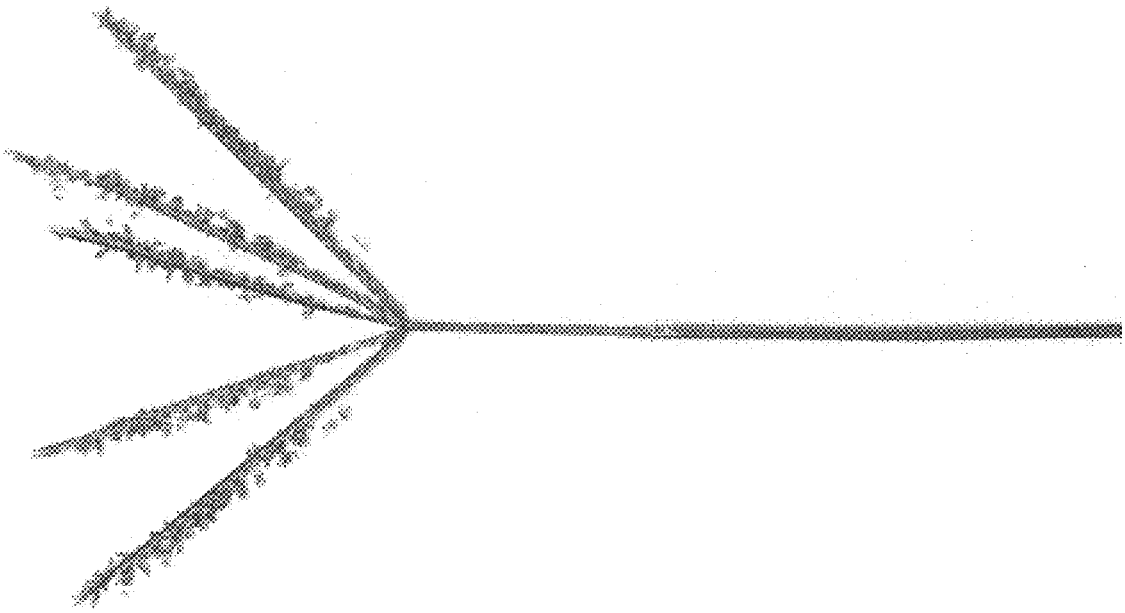
FIG. 4: Seedhead of "Ozark" bermudagrass at full maturity.
Figure 5:
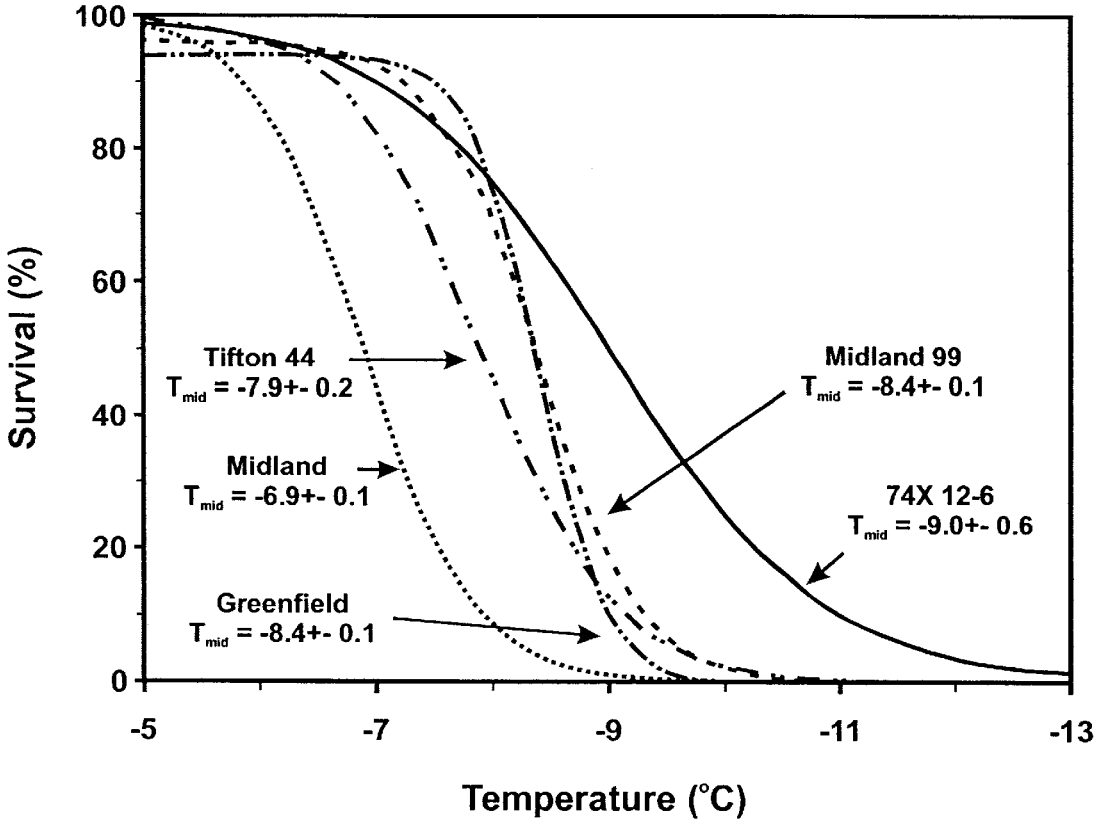
FIG. 5: Cold tolerance of five bermudagrass varieties subjected to freezing temperatures ranging from −5 to −13° C. in a controlled chamber.

"Ozark" has shown superior cold tolerance relative to previous bermudagrass varieties and has yielded well in the northern part of the bermudagrass belt. The superior adaptation, production and quality, for example, when grown in southern Missouri and Kansas thus make the variety unique among released bermudagrass varieties (FIG. 5). Based on its cold tolerance and stand persistence, "Ozark" is widely adaptive north of Springfield, Mo. (37° 14' N. 93° 23' W.) extending to Elsberry, Mo. (39° 10' N. 90° 47' W.). This includes the southern one-third of Missouri and Kansas, and statewide in Oklahoma and Arkansas. Bermudagrass is generally not able to grow in the colder regions of the state, but "Ozark" is highly tolerant to the differing cold temperature changes in the above listed region. A description of the variety is presented below.

A. Additional Characteristics of the Variety

The detailed botanical description presented herein was produced from observation of greenhouse grown "Ozark" plants with 5-weeks of accumulated growth (n=25 observations per trait).

Parentage: The variety is a clonally propagated $F_1$ hybrid of the cross of A9959×'Coastal'. Oklahoma accession A9959 (PI 253302) is a cold tolerant clonal bermudagrass introduction from Yugoslavia. Coastal is the $F_1$ hybrid of 'Tift' bermudagrass and a plant introduction from South Africa.

Propagation: Vegetative (asexual) by means of propagating plant crowns, stolons and rhizomes.

Growth habit: Tall, upright, warm season perennial grass that spreads by rhizomes and stolons to form a dense sod. Rhizomes are found at a depth of greater than 4 cm, allowing rapid regrowth and recovery from sprig harvesting. Stolons and rhizomes branch from nodes.

Mature leaf blade width (measured near base of leaf) emanating from $2^{nd}$ visible node from shoots: mean=4 mm range=3.8–4.2 mm.

Other leaf blade characteristics: The variety has long leaves compared to some other bermudagrass varieties. Leaves are glabrous on the abaxial and adaxial surfaces and taper toward the tip. Leaves have prominent parallel veins and serrated edges. Ligules are ciliate with hairs averaging 1 mm in length. Leaf characteristics vary slightly when under unusual fertility regimes as well as when under biotic or abiotic stress.

Description of upright shoots: Mean maximum height of shoots was 460 mm. For culms the mean diameter of widest internode dimension was 3.0 mm with a range of 2.6–3.2 mm. The mean diameter of the most narrow internode dimension was 2 mm with a range of 1.5 to 2.5 mm. The mean length of the $2^{nd}$ internode from shoot apex was 70 mm with a range of 65–74 mm. The mean number of internodes on culms ca. 460 mm tall was 5. The culm nodes were round to oval in shape and glabrous with a mean diameter of 3.2 mm and a range of 2.5–3.5 mm. The mean number of visible nodes on culms ca. 460 mm tall was 6. Color of culms=Munsell plant color chart designation of 7.5 GY 5/6.

Sheath: Open, shorter than the internode.

Ligule: A whitish fringe of hairs 1 mm in length.

Collar: Narrow and continuous.

Auricle: Absent.

Inflorescence: Produced less densely than most commercial bermudagrass varieties. When an inflorescence is produced, 4 to 6 digitate spikelets bear few, if any, viable seeds.

Plant color: The color designation of the variety is 7.5 GY 5/6 using a Munsell color chart rating (Munsell plant color chart, Macbeth Division of Kollmorgen Instruments Corporation, New Windsor, N.Y.).

Unmowed height: 75 to 100 cm.

Disease resistance: There have been no reports or observations of any unusual and/or severe insect or disease problems with the variety. Leaf disease has been minimal when other bermudagrass varieties showed severe infections.

Rooting: Produces vegetatively propagated roots from nodes of both stolons and rhizomes (nodal or adventitious roots), which are in the ground contact. The entire root system is comprised of adventitious roots that develop laterally and tend to become rudimentary unless the stolon or rhizome is severed. Once severed, the rudimentary roots rapidly develop to support the severed portion of the plant.

B. Growth Characteristics

Forage Yield for the variety has been evaluated in clipping trials at Mt. Vernon, Mo., (Southwest Missouri Research and Education Center; 37°06' N. 93°49' W.), Haskell (Eastern Research Station, 35°13' N. 95°08' W.), Chickasha (South Central Research Station, 35°03' N. 97°56' W.), and Ardmore (Noble Foundation, 34°10' N. 97°08' W.) Okla., Batesville, Ark., (Livestock and Forestry Branch Station, 35°46' N. 91°38' W.) and Parsons, Kans. (Southeast Agricultural Research Center 37°20' N. 95°15' W.).

In almost every yield trial conducted, "Ozark" has yielded as much or more forage than other varieties. In a three-year trial at Mt. Vernon, Mo., "Ozark" had an average yield of 9,867 kg $ha^{-1}$ (Table 1). In this trial, the three-year average yields of "Ozark" were equal to those for Midland 99, but 13% greater than Tifton 44, 31% greater than 'Hardie' and 38% greater than 'Guymon'. At Parsons, Kans., "Ozark" had outstanding yields, producing an average 14,986 kg $ha^{-1}$ of forage per year (Table 2). Although the yields were less during the first year of this trial, by the third (and final) year it produced significantly (18 to 40%) more forage than other varieties tested.

At Batesville, Ark., "Ozark" had a four-year average yield of 15,702 kg $ha^{-1}$. This yield from "Ozark" was similar to Tifton 44 and 'Greenfield', but 14% greater than Midland, 24% greater than 'World Feeder' and 37% greater than Guymon (Table 3). In trials conducted at Haskell and Chickasha, Okla., the variety yielded similarly to Tifton 44, Hardie and Midland 99, but produced significantly more forage than Midland, 'Quickstand', World Feeder and Greenfield (Tables 4 and 5). Yield tests conducted at the Noble Foundation, near Ardmore, Okla. showed that the variety produced four-year average yields that were similar to Coastal, Hardie, and Midland 99, but yielded 19% more forage than Tifton 44, 22% more than Midland, and 47% more than Quickstand (Table 6).

The excellent production of "Ozark" in Missouri, Kansas, Arkansas and Oklahoma is due in large part to its cold hardiness. In laboratory cold tolerance tests, "Ozark" had a $T_{mid}$ value of −9.0° C. (FIG. 5). This $T_{mid}$ value was significantly lower (i.e. indicating more cold tolerance) than any other variety tested including Midland 99, Greenfield, Midland, and Tifton 44. $T_{mid}$ values indicate the coldest temperature at which 50% of the plants survive.

The variety has survived well in a number of environments. Stands of the variety have not shown signs of winterkill at any location where yield testing has been conducted. Further, observation plots as far north as Elsberry, Mo. (39°10' N. 90°46' W.) have persisted more than six years where all other bermudagrass varieties showed signs of winterkill.

Overall the forage quality of "Ozark" has been similar or better than other high-yielding bermudagrass varieties. At Mt. Vernon, "Ozark" had acid detergent fiber (ADF), neutral detergent fiber (NDF) and crude protein (CP) values that were similar to Midland 99 and Tifton 44 (Table 7).

Forage quality of "Ozark" was also tested during 1995 at both Chickasha and Haskell, Okla. At Chickasha, "Ozark" had ADF, NDF and CP values that were equal to the highest yielding varieties in the trial (Tifton 44, Hardie and Midland 99) except that it had 10 g $kg^{-1}$ less ADF than Tifton 44 (Table 8). At Haskell, "Ozark" has less ADF and NDF than the other high-yielding varieties (Midland 99, Hardie, and Tifton 44) (Table 9). The crude protein concentration of "Ozark" was similar to all the other varieties tested at Haskell.

TABLE 1

Annual and three-year average forage yield of five bermudagrass varieties grown at the Southwest Missouri Research and Education Center, near Mt. Vernon, Missouri

| Variety | 1996 | 1997 | 1998 | Average |
|---|---|---|---|---|
| | | kg $ha^{-1}$ | | |
| Ozark | 6,707 | 11,189 | 11,704 | 9,867 |
| Midland 99 | 5,980 | 11,005 | 11,119 | 9,368 |
| Tifton 44 | 5,615 | 10,219 | 9,931 | 8,588 |
| Hardie | 4,580 | 7,622 | 8,366 | 6,856 |
| Guymon | 4,116 | 7,233 | 7,048 | 6,132 |
| Average | 5,400 | 9,454 | 9,634 | 8,162 |
| LSD (0.05) | 1,244 | 1,059 | 1,532 | 992 |

TABLE 2

Annual and 3-year average yield of 6 bermudagrass varieties grown at the Mound Valley Unit, Southeast Agricultural Research Center, near Parsons, Kansas

| Variety | 1993 | 1994 | 1995 | Average |
|---|---|---|---|---|
| | | kg $ha^{-1}$ | | |
| Ozark | 10,304 | 18,144 | 16,509 | 14,986 |
| Hardie | 13,373 | 17,584 | 13,530 | 14,829 |
| Tifton 44 | 11,715 | 15,792 | 12,970 | 13,492 |
| Midland | 9,856 | 13,171 | 10,886 | 11,305 |
| Greenfield | 10,170 | 9,587 | 10,774 | 10,177 |
| World Feeder | 9,206 | 9,632 | 9,946 | 9,595 |
| Average | 10,771 | 13,985 | 12,436 | 12,397 |
| LSD (0.05) | 1,322 | 1,770 | 1,837 | |

TABLE 3

Annual and 4-year forage yield of 6 bermudagrass varieties grown at the Livestock and Forestry

| Variety | 1995 | 1996 | 1997 | 1998 | Average |
|---|---|---|---|---|---|
| | | | kg $ha^{-1}$ | | |
| Tifton 44 | 18,637 | 13,530 | 1,837 | 18,122 | 16,442 |
| Ozark | 18,144 | 13,104 | 13,709 | 17,853 | 15,702 |
| Greenfield | 18,637 | 11,962 | 14,224 | 14,448 | 14,818 |
| Midland | 16,755 | 9,050 | 13,619 | 14,470 | 13,474 |
| World Feeder | 15,501 | 7,706 | 12,768 | 11,917 | 11,973 |
| Guymon | 13,574 | 7,146 | 8,355 | 10,192 | 9,817 |
| Average | 16,875 | 10,416 | 13,026 | 14,500 | 13,704 |
| LSD (0.05) | 3,203 | 2,733 | 2,016 | 2,262 | 1,792 |

TABLE 4

Annual and 4-year average forage yield of 8 bermudagrass varieties grown at the South Central Research Station, near Chickasha, Oklahoma

| Variety | 1995 | 1996 | 1997 | 1998 | Average |
|---|---|---|---|---|---|
| | | | kg $ha^{-1}$ | | |
| Tifton 44 | 26,006 | 25,446 | 21,213 | 20,093 | 23,190 |
| Hardie | 28,829 | 26,006 | 18,525 | 16,083 | 22,361 |
| Ozark | 27,059 | 22,624 | 18,502 | 16,710 | 21,224 |
| Midland 99 | 25,693 | 22,736 | 19,286 | 17,002 | 21,179 |
| Midland | 23,834 | 20,362 | 16,867 | 12,275 | 18,335 |
| Quickstand | 20,586 | 19,869 | 11,738 | 6,115 | 14,577 |
| World Feeder | 18,256 | 16,016 | 9,968 | 5,802 | 12,511 |
| Greenfield | 16,621 | 16,934 | 11,088 | 5,533 | 12,544 |
| Average | 23,360 | 21,249 | 15,898 | 12,452 | 18,240 |
| LSD (0.05) | 3,539 | 3,002 | 2,509 | 2,778 | 2,106 |

TABLE 5

Annual and 3-year average forage yield of 8 bermudagrass grown at the Eastern Research Station, near Haskell, Oklahoma

| Variety | 1995 | 1996 | 1997 | Average |
|---|---|---|---|---|
| | | kg ha$^{-1}$ | | |
| Midland 99 | 24,901 | 21,146 | 20,675 | 22,241 |
| Hardie | 23,811 | 18,973 | 21,347 | 21,377 |
| Tifton 44 | 22,938 | 19,914 | 20,807 | 21,220 |
| Ozark | 22,557 | 20,115 | 20,899 | 21,290 |
| Midland | 21,011 | 17,584 | 17,181 | 18,592 |
| Quickstand | 20,070 | 17,069 | 14,314 | 17,151 |
| Greenfield | 18,928 | 13,709 | 15,501 | 16,046 |
| World Feeder | 17,046 | 15,165 | 15,322 | 15,844 |
| Average | 21,408 | 17,959 | 18,256 | 19,208 |
| LSD (0.05) | 1,008 | 1,949 | 2,419 | 1,613 |

TABLE 6

Annual and 4-year average forage yield of 7 bermudagrass varieties grown at the Noble Foundation, near Ardmore, Oklahoma

| Variety | 1996 | 1997 | 1998 | 1999 | Average |
|---|---|---|---|---|---|
| | | | kg ha$^{-1}$ | | |
| Coastal | 5,750 | 7,056 | 13,526 | 10,619 | 9,238 |
| Ozark | 7,195 | 5,812 | 12,491 | 10,927 | 9,106 |
| Hardie | 7,499 | 6,193 | 10,917 | 10,759 | 8,842 |
| Midland 99 | 6,056 | 5,994 | 11,877 | 9,801 | 8,432 |
| Tifton 44 | 5,811 | 5,363 | 9,826 | 8,652 | 7,413 |
| Midland | 6,154 | 4,239 | 9,178 | 8,679 | 7,062 |
| Quickstand | 4,416 | 1,960 | 6,642 | 6,324 | 4,835 |
| Average | 6,126 | 5,231 | 10,637 | 9,394 | 7,847 |
| LSD (0.05) | 1,570 | 1,698 | 2,272 | 1,430 | 1,578 |

TABLE 7

Three-year average (1996–1998) of acid detergent fiber (ADF), neutral detergent fiber (NDF), and crude protein of 5 bermudagrass varieties grown at the Southwest Missouri Research and Education Center, near Mt. Vernon, Missouri

| Variety | Acid Detergent Fiber | Neutral Detergent Fiber | Crude Protein |
|---|---|---|---|
| | | g kg$^{-1}$ | |
| Guyman | 262 | 553 | 192 |
| Hardie | 282 | 537 | 188 |
| Tifton 44 | 271 | 589 | 178 |
| Midland 99 | 270 | 573 | 177 |
| Ozark | 271 | 575 | 177 |
| Average | 271 | 565 | 182 |
| LSD (0.05) | 6.1 | 19.0 | 7.3 |

TABLE 8

Acid detergent fiber (ADF), neutral detergent fiber (NDF), and crude protein during 1995 of eight bermudagrass varieties grown at the South Central Research Station, near Chickasha, Oklahoma

| Variety | Acid Detergent Fiber | Neutral Detergent Fiber | Crude Protein |
|---|---|---|---|
| | | g kg$^{-1}$ | |
| Tifton 44 | 383 | 724 | 130 |
| Hardie | 376 | 711 | 129 |
| Ozark | 373 | 703 | 128 |
| Midland 99 | 369 | 714 | 126 |
| Midland | 374 | 713 | 130 |
| Quickstand | 366 | 704 | 119 |
| World Feeder | 359 | 714 | 121 |
| Greenfield | 360 | 683 | 128 |
| Average | 370 | 710 | 126 |
| LSD (0.05) | 9 | 20 | NS |

TABLE 9

Acid detergent fiber (ADF), neutral detergent fiber (NDF), and crude protein during 1995 of eight bermudagrass varieties grown at the Eastern Research Station, near Haskell, Oklahoma

| Variety | Acid Detergent Fiber | Neutral Detergent Fiber | Crude Protein |
|---|---|---|---|
| | | g kg$^{-1}$ | |
| Midland 99 | 389 | 722 | 122 |
| Hardie | 395 | 731 | 112 |
| Tifton 44 | 401 | 755 | 115 |
| Ozark | 376 | 712 | 125 |
| Midland | 384 | 726 | 124 |
| Quickstand | 397 | 740 | 113 |
| Greenfield | 380 | 713 | 132 |
| World Feeder | 375 | 734 | 121 |
| Average | 389 | 730 | 120 |
| LSD (0.05) | 12 | 13 | NS |

What is claimed is:

1. A new and distinct hybrid bermudagrass plant as illustrated and described herein.

* * * * *